(12) United States Patent
Park et al.

(10) Patent No.: US 10,898,310 B2
(45) Date of Patent: Jan. 26, 2021

(54) DEVICE FOR DELIVERING GRAFTS AT A SURGICAL SITE AND METHOD

(71) Applicant: Park Surgical Innovations, LLC, Peachtree Corners, GA (US)

(72) Inventors: David D. Park, Peachtree Corners, GA (US); Ashley B. Hancock, Atlanta, GA (US); Byron F. Smith, Nashville, TN (US); Tanner Hargens, Brentwood, TN (US)

( * ) Notice: Subject to any disclaimer, the term of this patent is extended or adjusted under 35 U.S.C. 154(b) by 180 days.

(21) Appl. No.: 16/029,447

(22) Filed: Jul. 6, 2018

(65) Prior Publication Data

US 2019/0008622 A1    Jan. 10, 2019

Related U.S. Application Data

(60) Provisional application No. 62/529,262, filed on Jul. 6, 2017.

(51) Int. Cl.
*A61F 2/00* (2006.01)
*A61B 17/34* (2006.01)
(Continued)

(52) U.S. Cl.
CPC ........ *A61F 2/0063* (2013.01); *A61B 17/3468* (2013.01); *A61B 17/0057* (2013.01);
(Continued)

(58) Field of Classification Search
CPC ........... A61F 2/0063; A61F 2002/0072; A61B 17/00234; A61B 17/2905;
(Continued)

(56) References Cited

U.S. PATENT DOCUMENTS 5,147,316 A   9/1992  Castillenti
5,234,443 A * 8/1993  Phan ............... A61B 17/0469
                                                    606/144
(Continued)

FOREIGN PATENT DOCUMENTS

EP    1224919    7/2002
EP    1408846    3/2012
(Continued)

OTHER PUBLICATIONS

Theodore R. Kucklick; Basics of Catheter Assemby; The Medical Device R&D Handbook, Second Edition; 2013; pp. 107-125.
(Continued)

*Primary Examiner* — Katherine H Schwiker
*Assistant Examiner* — Alexis D Amechi
(74) *Attorney, Agent, or Firm* — B. Craig Killough; Riley Pope & Laney

(57) ABSTRACT

A device and method for delivering a synthetic mesh or graft for anatomical repair at a defect site. A plurality of flexible arms is connected to the synthetic mesh or graft. Grasping jaws are individually controlled at or near a proximal end of the device for connection of the graft and release of the graft at the surgical site. The flexible arms, with graft attached are positioned through a surgical incision to the defect site. An actuator positions the flexible arms to assume a radial array at the surgical site, unfolding and spreading the graft for attachment. The length of each flexible arm is individually adjustable to adapt to the size and shape of the graft selected for installation at the defect site to repair the defect.

23 Claims, 16 Drawing Sheets

(51) Int. Cl.
*A61B 17/00* (2006.01)
*A61B 90/00* (2016.01)

(52) U.S. Cl.
CPC ............ *A61B 2017/0042* (2013.01); *A61B 2017/00305* (2013.01); *A61B 2017/00323* (2013.01); *A61B 2017/00336* (2013.01); *A61B 2017/00367* (2013.01); *A61B 2090/037* (2016.02); *A61F 2002/0072* (2013.01)

(58) Field of Classification Search
CPC .... A61B 2017/2906; A61B 2017/2908; A61B 2017/291; A61B 2017/00336; A61B 17/0057; A61B 17/29; A61B 2017/3445; A61B 2017/3447; A61B 2017/3441; A61B 2017/3466; A61B 17/22031; A61B 17/221
See application file for complete search history.

(56) References Cited

U.S. PATENT DOCUMENTS

| | | | |
|---|---|---|---|
| 5,312,391 A * | 5/1994 | Wilk | A61B 17/00234 604/264 |
| 5,379,754 A | 1/1995 | Tovey et al. | |
| 5,395,367 A * | 3/1995 | Wilk | A61B 17/00234 606/1 |
| 5,405,360 A | 4/1995 | Tovey | |
| 5,755,713 A * | 5/1998 | Bilof | A61B 17/00234 600/104 |
| 5,957,939 A | 9/1999 | Heaven et al. | |
| 6,425,924 B1 | 7/2002 | Rousseau | |
| 6,478,803 B1 | 11/2002 | Kapec et al. | |
| 6,669,735 B1 | 12/2003 | Pelissier | |
| 7,662,112 B2 | 2/2010 | Zamierowski et al. | |
| 7,947,054 B2 | 5/2011 | Eldar et al. | |
| 7,963,992 B2 | 6/2011 | Cauthen, III et al. | |
| 8,097,008 B2 | 1/2012 | Henderson | |
| 8,518,024 B2 * | 8/2013 | Williams | A61B 1/00052 606/1 |
| 8,579,989 B2 | 11/2013 | Leahy | |
| 8,616,460 B2 | 12/2013 | Kurtz et al. | |
| 8,641,699 B2 | 2/2014 | Hansen | |
| 9,339,365 B2 | 5/2016 | Park et al. | |
| 9,717,524 B2 * | 8/2017 | Hayashida | A61B 17/29 |
| 2006/0015142 A1 | 1/2006 | Malazgirt | |
| 2007/0185506 A1 | 8/2007 | Jackson | |
| 2008/0071343 A1* | 3/2008 | Mayberry | A61F 2/954 623/1.11 |
| 2008/0195121 A1 | 8/2008 | Elder et al. | |
| 2009/0254103 A1 | 10/2009 | Deutsch | |
| 2010/0069930 A1 | 3/2010 | Roslin et al. | |
| 2010/0069947 A1 | 3/2010 | Sholev et al. | |
| 2010/0130850 A1 | 5/2010 | Pakter | |
| 2010/0179579 A1 | 7/2010 | Halevy | |
| 2011/0015491 A1* | 1/2011 | Ravikumar | A61B 1/32 600/233 |
| 2011/0054500 A1 | 3/2011 | Levin et al. | |
| 2011/0184459 A1 | 7/2011 | Malkowski et al. | |
| 2011/0196392 A1 | 8/2011 | Saadat et al. | |
| 2012/0016409 A1 | 1/2012 | Sherwinter et al. | |
| 2012/0078244 A1* | 3/2012 | Worrell | A61B 17/07207 606/33 |
| 2012/0095451 A1 | 4/2012 | Hegeman et al. | |
| 2012/0190924 A1 | 7/2012 | Tseng | |
| 2013/0012958 A1 | 1/2013 | Marczyk et al. | |
| 2014/0107675 A1 | 4/2014 | Hansen | |
| 2014/0276914 A1* | 9/2014 | Hayashida | A61B 17/08 606/119 |
| 2016/0051280 A1* | 2/2016 | Dejima | A61B 1/00087 600/114 |

FOREIGN PATENT DOCUMENTS

| | | |
|---|---|---|
| EP | 2617350 | 12/2014 |
| EP | 2729077 | 7/2018 |
| WO | WO 2012128591 | 12/2012 |
| WO | WO 2013009699 | 1/2013 |
| WO | WO 2013154700 | 10/2013 |

OTHER PUBLICATIONS

Filip Jelinek, Ewout A. Arkenbout, Paul W.J. Henselmans, Rob Pessers, Paul Breedveld; Classification of Joints Used in Steerable Instruments for Minimally Invasive Surgery—A Review of the State of the Art; Journal of Medical Devices, Mar. 2015, vol. 9; pp. 010801-1-010801-11.

* cited by examiner

DEVICE FOR DELIVERING GRAFTS AT A SURGICAL SITE AND METHOD

Applicant claims the benefit of U.S. Provisional Application Ser. No. 62/529,262 filed Jul. 6, 2017.

BACKGROUND OF THE INVENTION

Biological grafts and synthetic mesh are used to repair anatomical defects, such as hernias. Delivery of the mesh or graft into body cavities either requires invasive surgery, or heretofore unsatisfactory laparoscopic methods.

Hernias are structural defects most commonly involving the musculofascial tissues of the abdominal and pelvic regions within the human body. Most hernias eventually require surgical repair. Surgical repair of ventral incisional hernias may be accomplished via an "open method." This method involves making a sizable incision directly over the tissue defect, separating the contents of the hernia away from the musculofascial defect, and repairing the defect primarily using sutures, or more commonly, sewing a graft to the defect edge in tension-free manner. This is done in an effort to minimize the recurrence of hernia formation which may occur with some frequency. The recurrence may be due to multiple factors including general health of the patient, surgical technique, and types of mesh or graft utilized. Overall, this traditional method is effective, but also often involves more pain, long periods of disability following the surgery, higher perioperative infection rates, and an established hernia recurrence rate.

Alternatively, ventral incisional hernias may be repaired using the "laparoscopic method." However, this method has its own set of major shortcomings principally related to higher degree of difficulty in performing this procedure. One of the major challenges involve graft introduction into the abdominal cavity. Typically, a graft is rolled tightly into a cylindrical configuration and subsequently, pushed/pulled through the trocar which can be both time consuming and frustrating, especially when a larger graft is needed to cover the defect. This maneuver can also damage the graft during the delivery due to excessive force used or needed during the delivery process. Some surgeons also elect to place multiple sutures within the periphery of the graft for transfascial securement. This is often done prior to introduction of the graft. Once delivered into the abdominal cavity, the rolled graft/suture combination is unrolled, sutures isolated into respective corresponding abdominal quadrants, and the graft is centered over the defect prior to fixation. These steps are often very challenging and frustrating to accomplish in an efficient manner due to the pliable property of the graft and sutures which is a desired characteristic.

SUMMARY OF THE INVENTION

The present invention is a device and method for delivering a synthetic mesh or graft for anatomical repair at a defect site. A plurality of flexible arms is connected to the synthetic mesh or graft. Grasping jaws are individually controlled at or near a proximal end of the device for connection of the graft and release of the graft at the surgical site. The flexible arms, with graft attached are positioned through a surgical incision to the defect site. An actuator positions the flexible arms to assume a radial array at the surgical site, unfolding and spreading the graft for attachment. The length of each flexible arm is individually adjustable to adapt to the size and shape of the graft selected for installation at the defect site to repair the defect.

BRIEF DESCRIPTIONS OF THE DRAWINGS

Figure 6A:
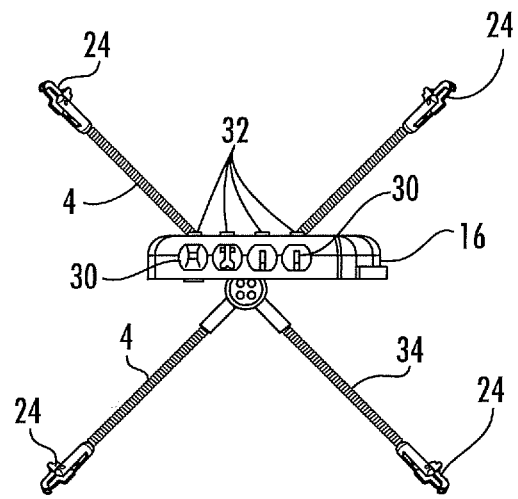
FIG. 6A is an elevation of an embodiment of the invention taken from a proximal end of the invention.
Figure 6B:
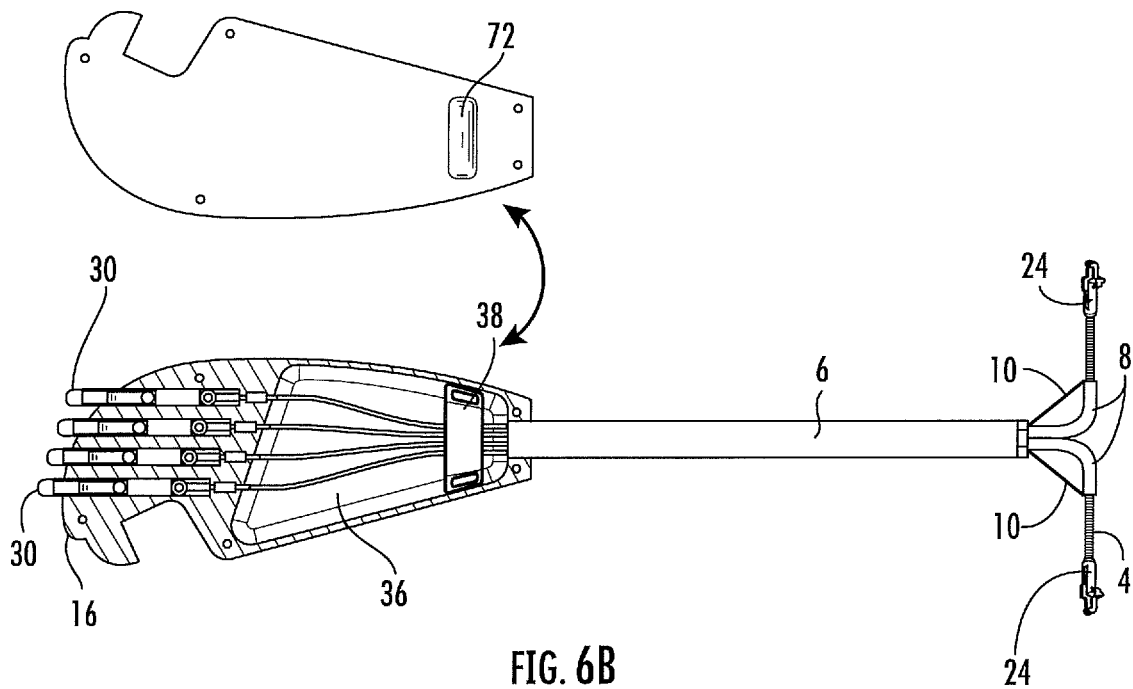

FIG. 6B demonstrates a cover for the housing removed from the device.

Figure 7:
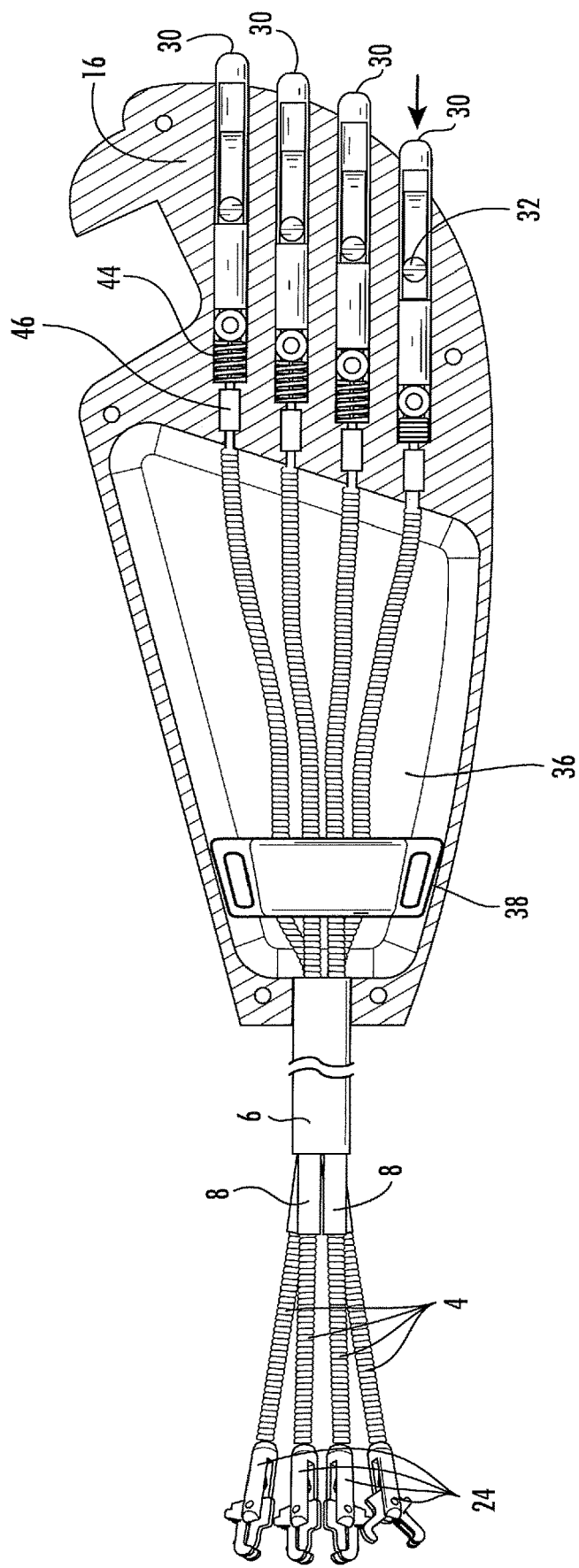

FIG. 7 is an elevation of one side of an embodiment of the invention with the cover removed from housing 16.

Figure 8:
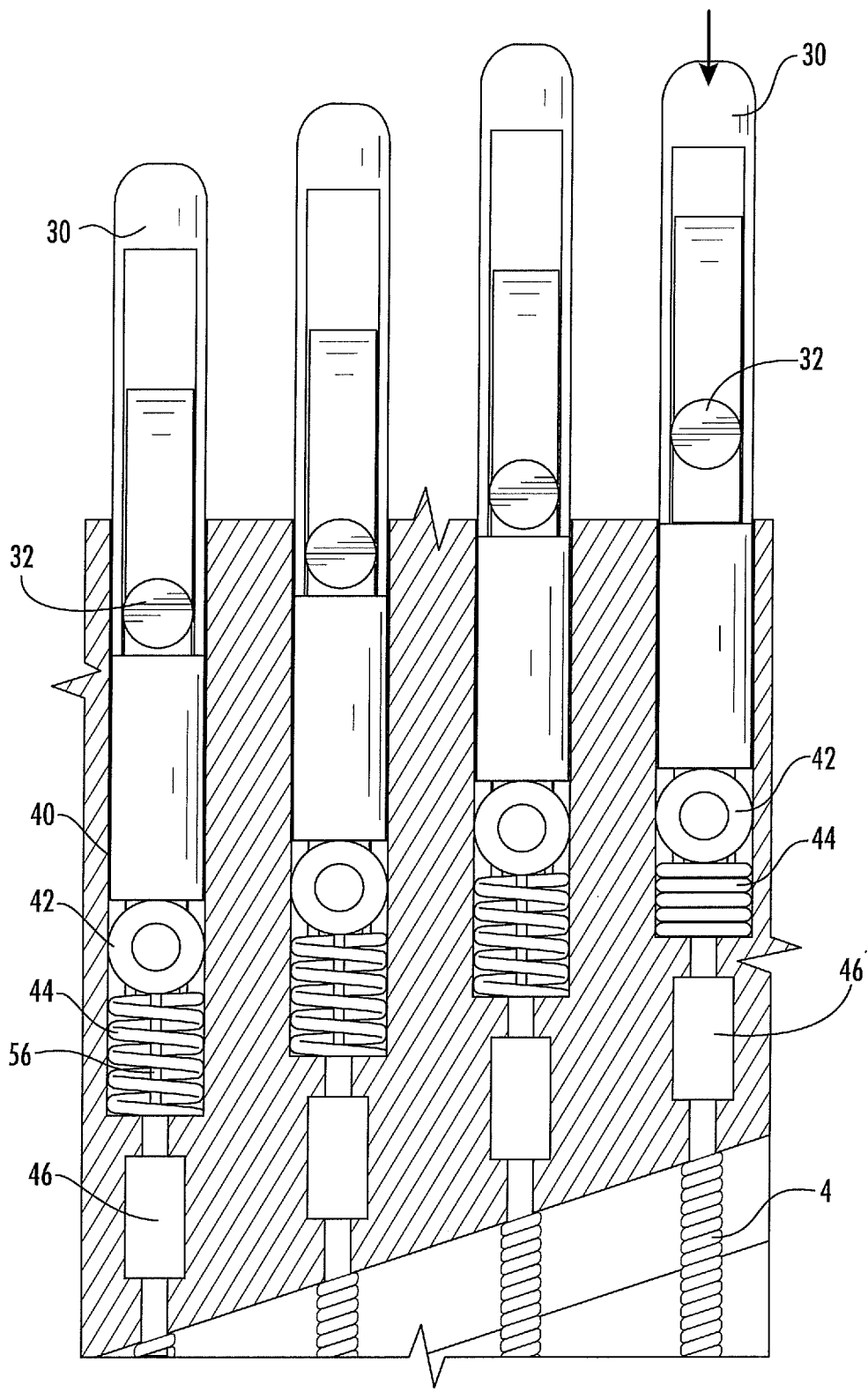

FIG. 8 is an enlarged isolation of a portion of the actuators for grasping jaws 24.

Figure 9:
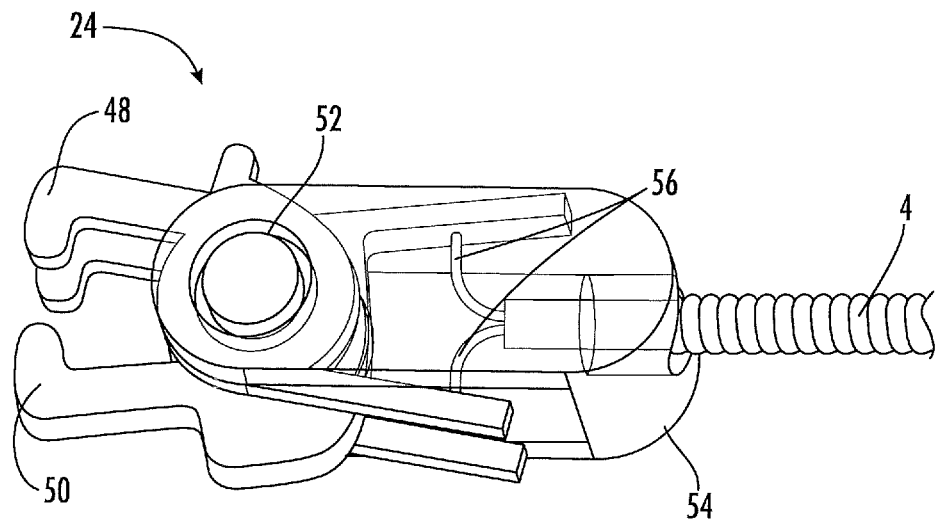

FIG. 9 is an isolation of an embodiment of a grasping jaw 24.

Figure 10A:
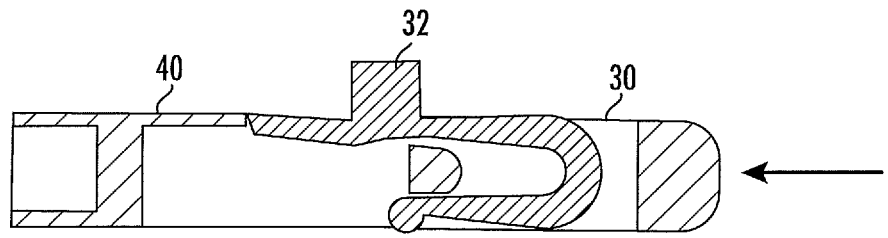
Figure 10B:
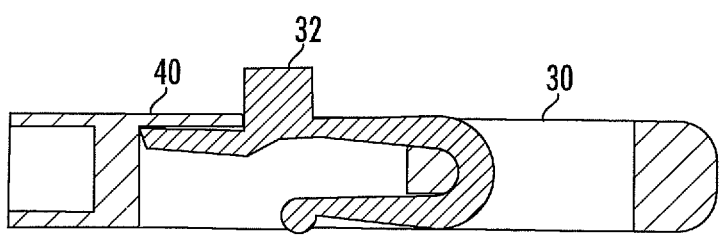

FIG. 10A and FIG. 10B are isolations of a portion of the actuator for the grasping jaws sectioned to demonstrate the action of release button 32.

Figure 11A:
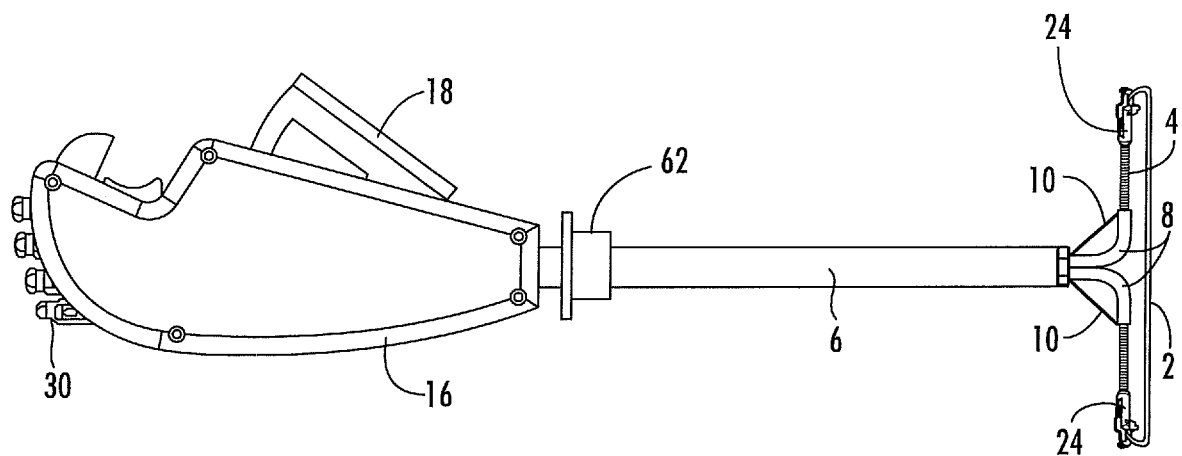

FIG. 11A shows the device according to an embodiment of the invention with a graft affixed to it.

Figure 11B:
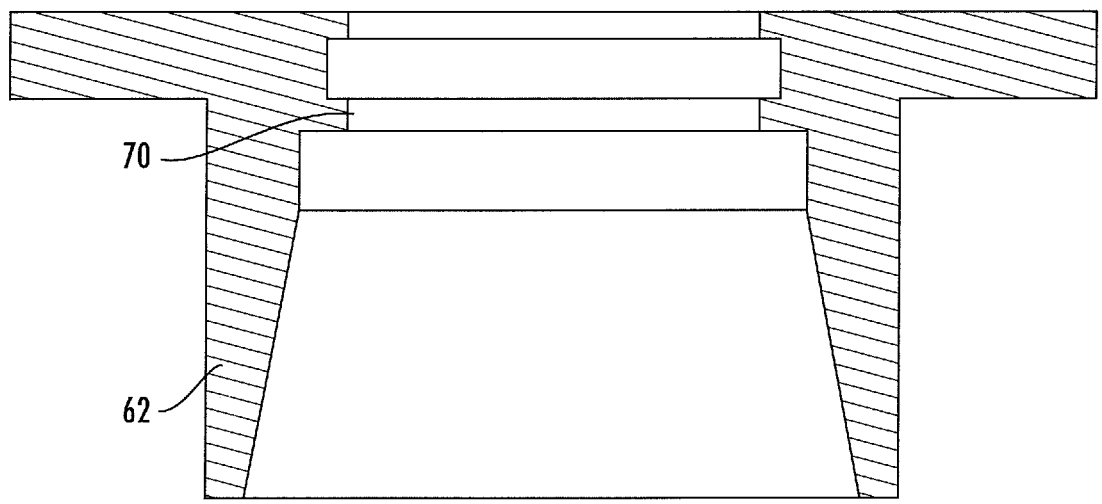

FIG. 11B is a side sectioned view of a seal that slidably attaches to a shaft of the device for sealing a trocar.

Figure 12:
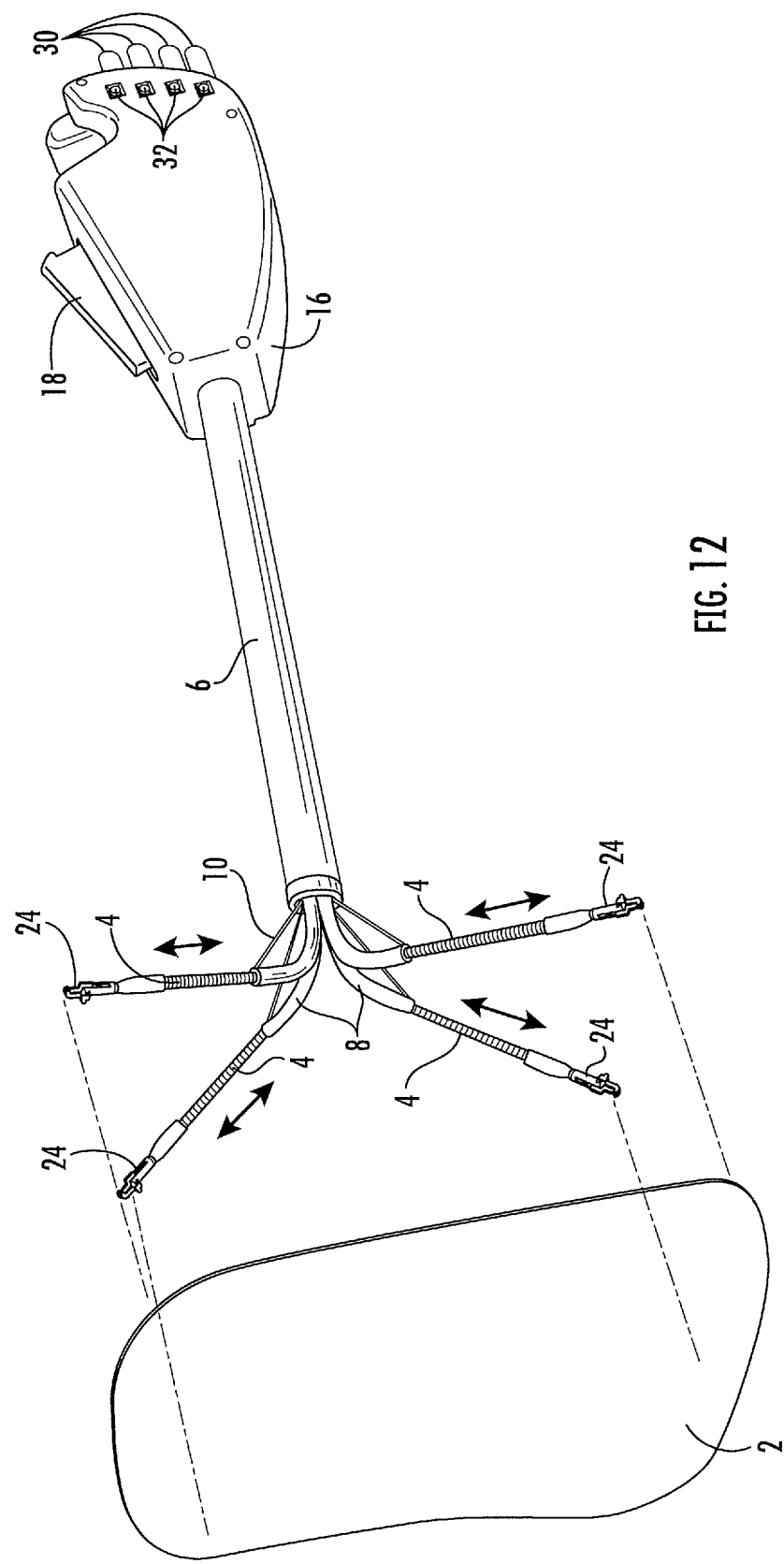

FIG. 12 demonstrates attachment of the graft to the embodiment of the device as shown in the drawing figures.

Figure 13A:
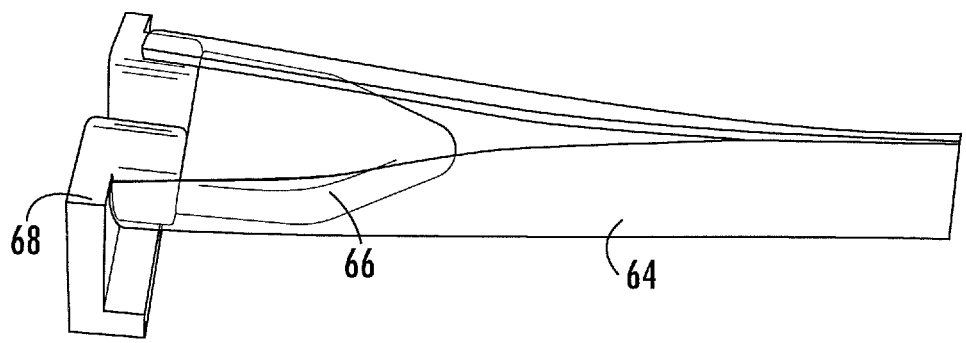

FIG. 13A shows a sheath that covers the graft to facilitate insertion of the graft and a portion of the device through a trocar and into the surgical site.

Figure 13B:
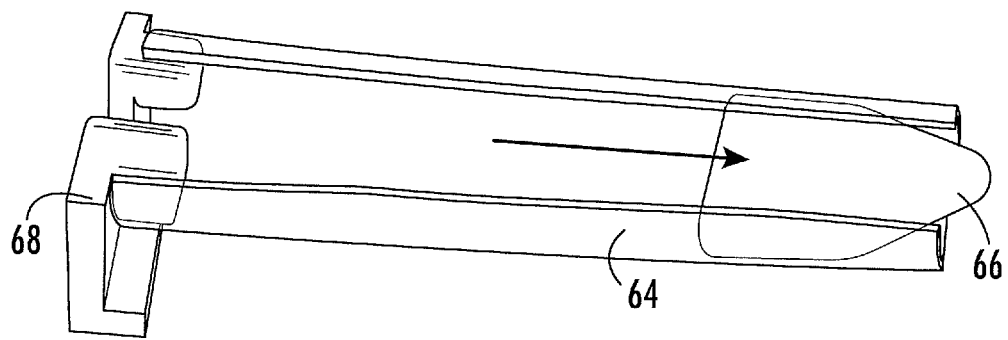

FIG. 13B demonstrates a step of opening of a split in the sheath for insertion of the device with graft into the sheath.

Figure 13C:
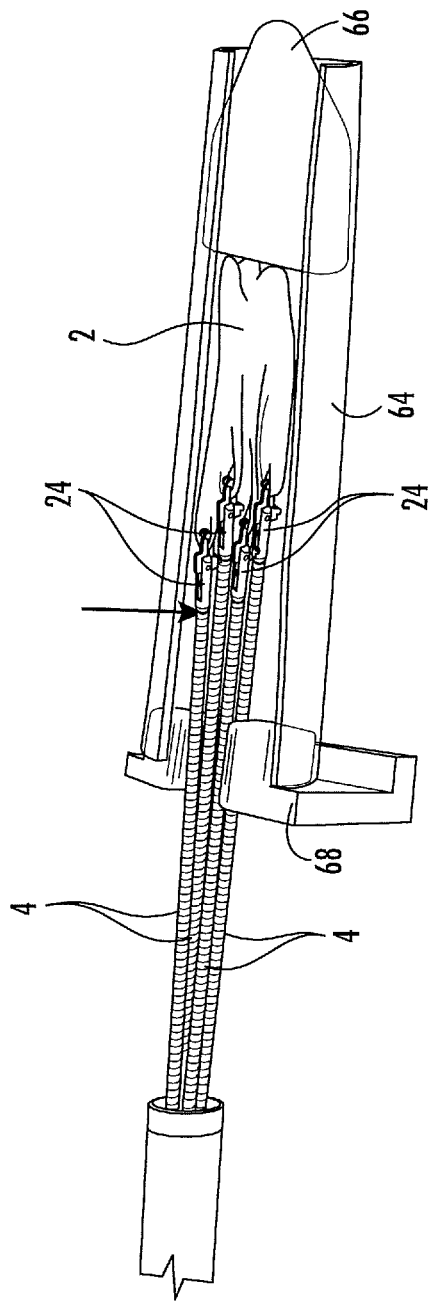

FIG. 13C shows the step of positioning the device with graft into the sheath.

Figure 13D:
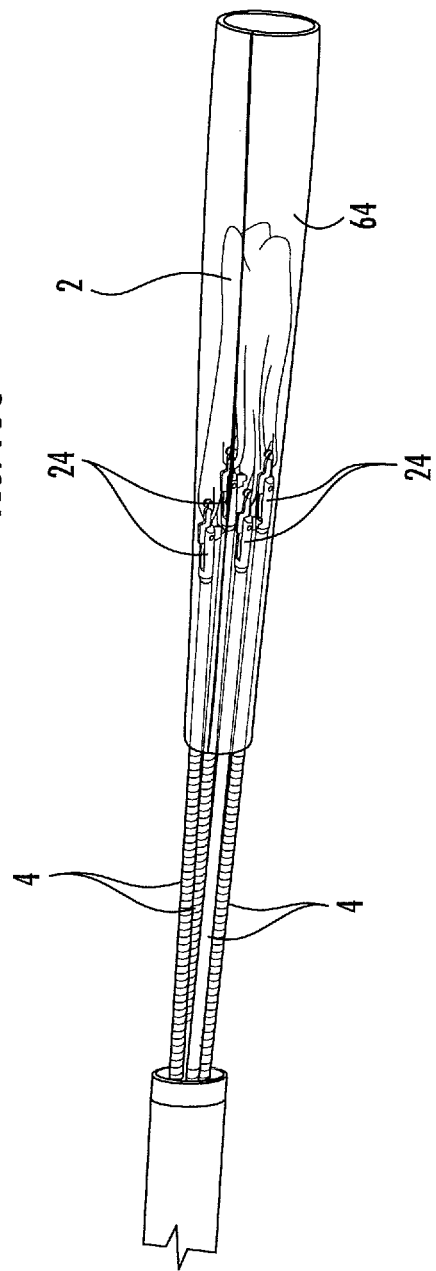

FIG. 13D shows the device with graft in the sheath and surrounding the sheath.

Figure 14A:
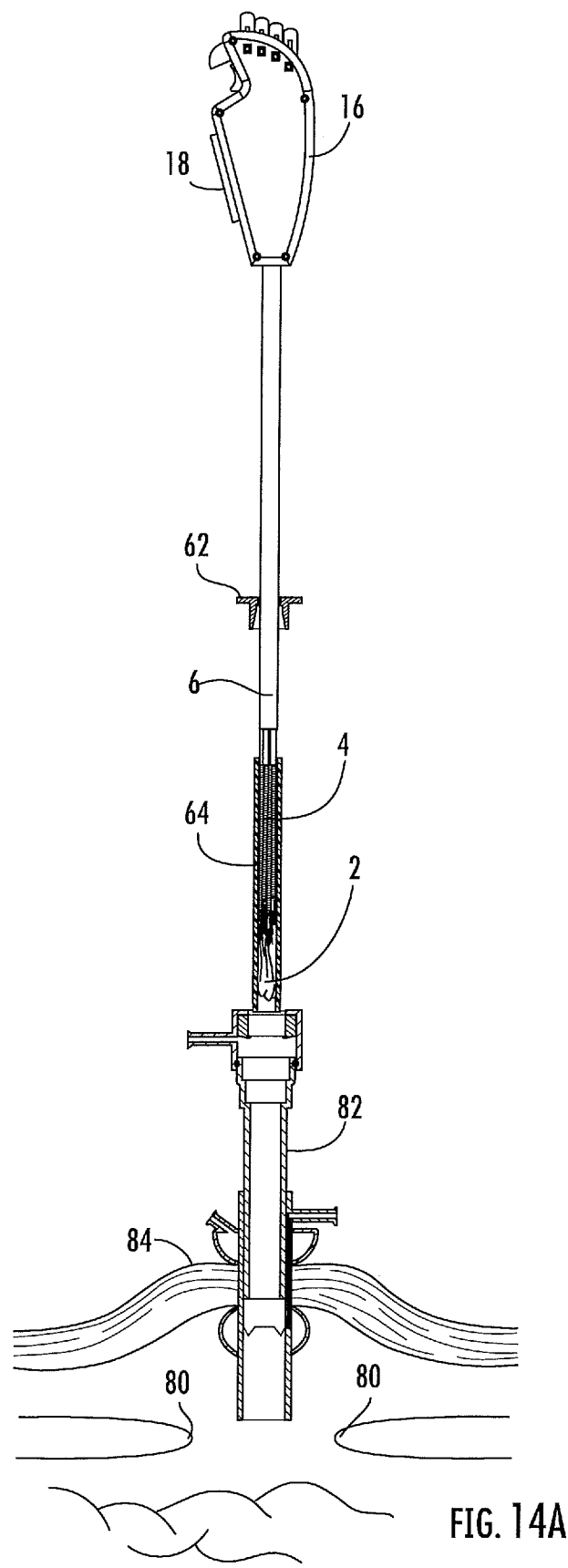
Figure 14B:
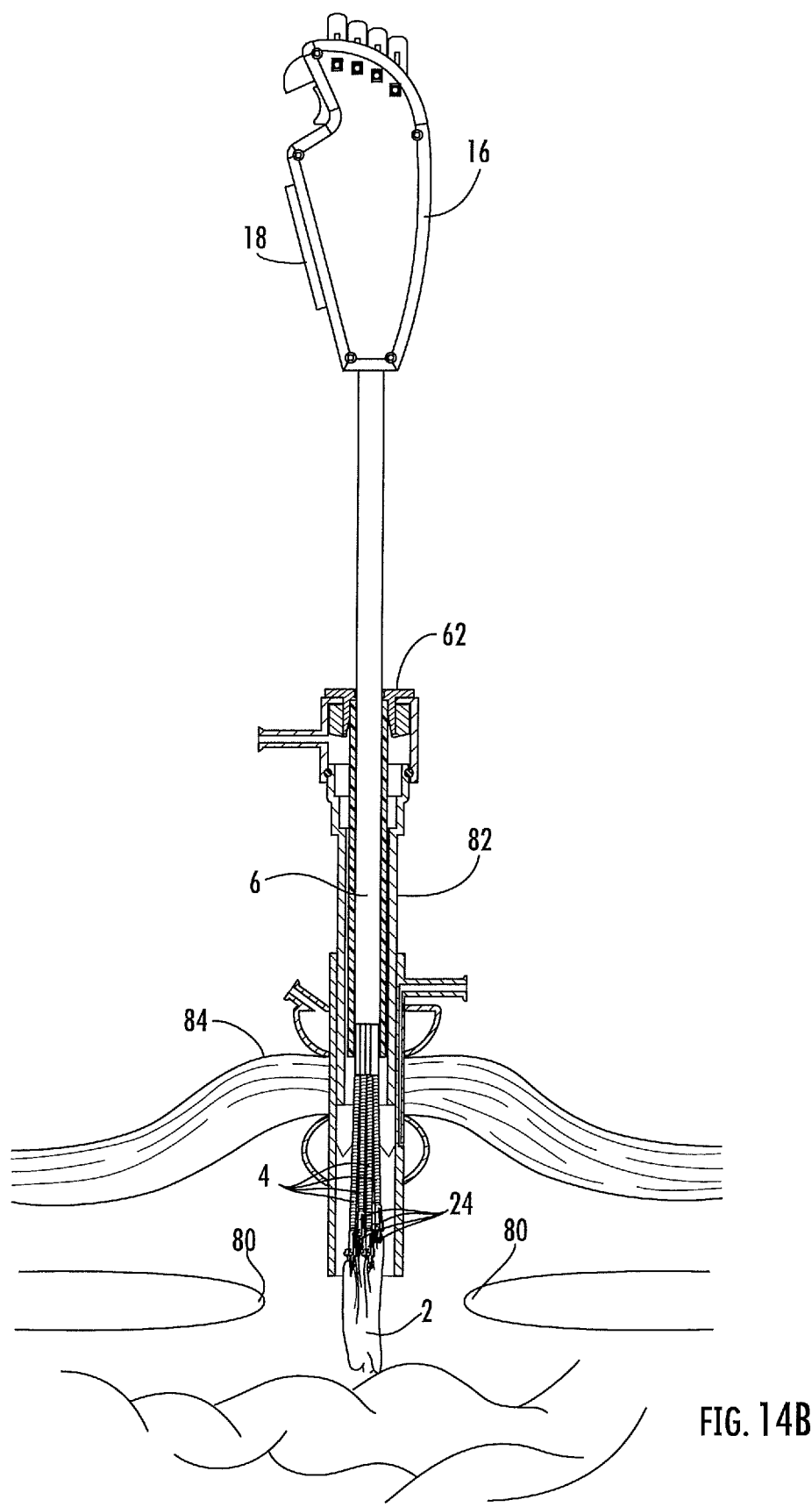
Figure 14C:
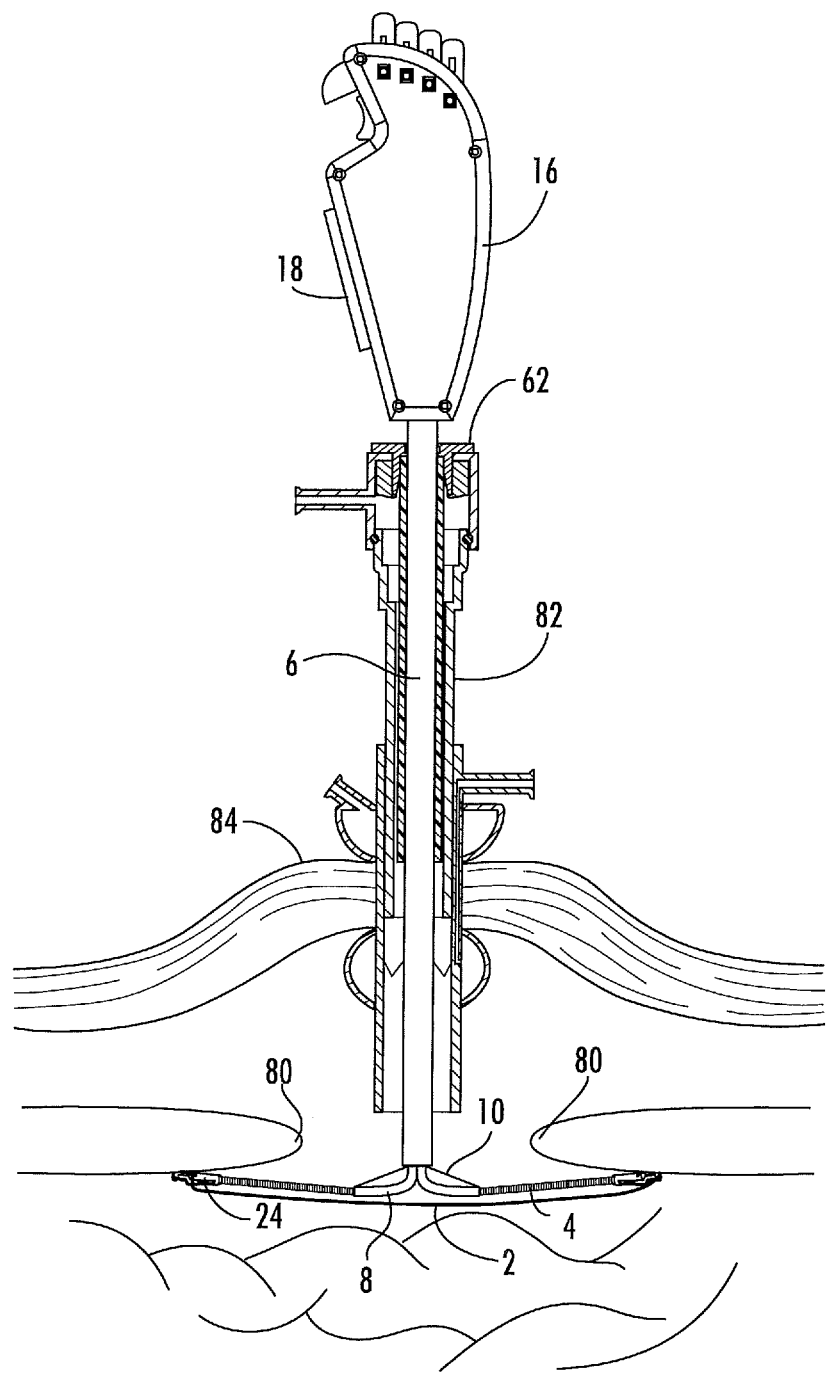

FIGS. 14A-14C demonstrate deployment of the graft through a trocar and into the surgical site using the device according to an embodiment of the device.

DESCRIPTION OF PREFERRED EMBODIMENTS

Figure 1:
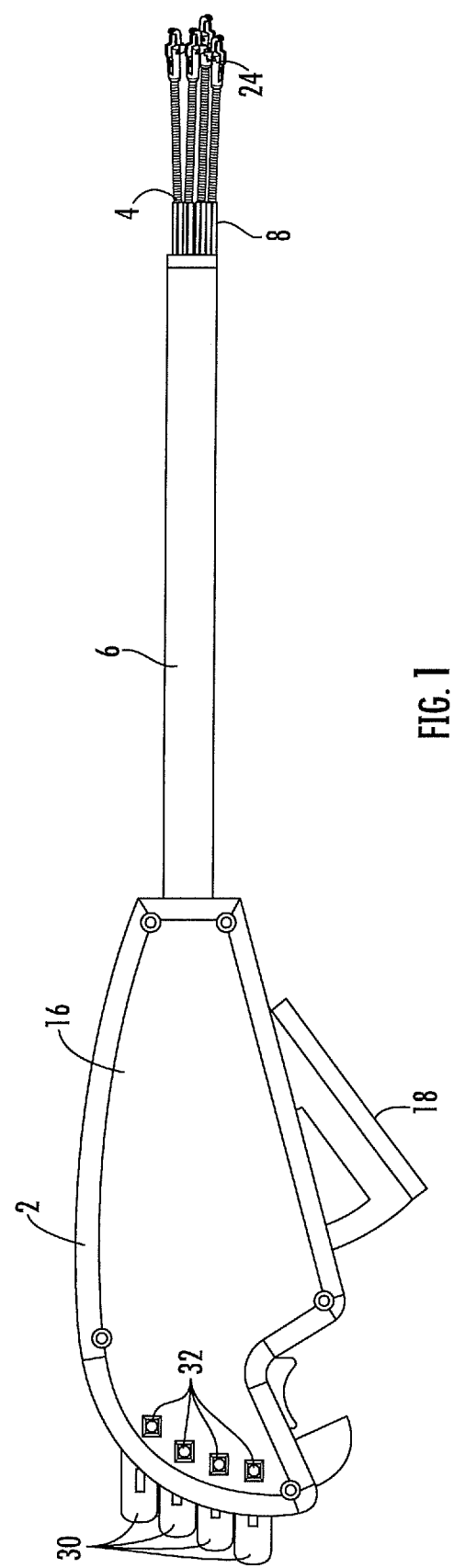
FIG. 1 is a side elevation of an embodiment of the invention.

Turning now to the drawing figures, FIG. 1 shows an embodiment of a delivery device for delivering a graft or synthetic mesh for attachment to tissue. The term "graft" is used herein to indicate either a graft formed of biological material, or a synthetic mesh. The graft is connected to a plurality of flexible arms 4. The flexible arms as shown in FIG. 1 extend from in a tube or shaft 6. The flexible arms are shown as being generally parallel to a central axis of the shaft. Since the flexible arms are flexible, some bending of the flexible arms means that they may not be strictly parallel, but are generally parallel, to the axis of travel of the rack 22 of the actuator while the flexible arms are in the position shown in FIG. 1.

Figure 2:
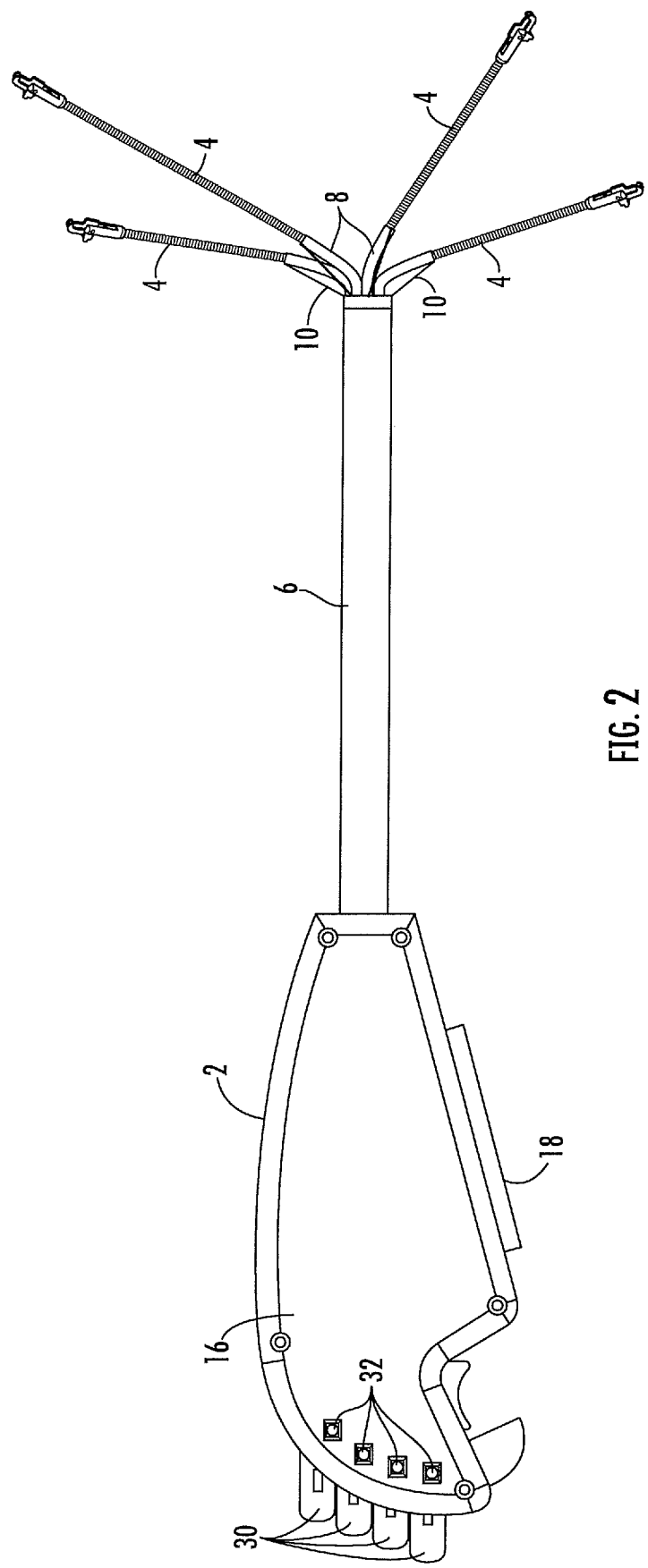
FIG. 2 shows the embodiment of FIG. 1 with the flexible arms 4 in a deployed position.

FIG. 1 and FIG. 2 show the device for delivery of graft for attachment to tissue, according to an embodiment, prior to deployment of the graft. Control wires 10 are actuated to pull against sleeves 8 that surround a portion of the flexible arms 4. The control wires extend through the shaft but may be external to the flexible arms as shown in FIG. 1 and FIG. 2, or they may be internal to the flexible arms. The control wires are connected to the sleeves at or near a distal end of the sleeves and control wires. In a preferred embodiment, each of the plurality of control wires is associated with one of the plurality of the flexible arms. Upon actuation, the control wires pull against the sleeves at the point of attachment to the sleeves. The force of the control wires acting on the sleeves pulls the flexible arms from the position shown in FIG. 1 and into a radial array as demonstrated in FIG. 2. The control wires are preferred to be nitinol wires, but the control wires may be formed of other metals, or plastics, textile materials or polymers, or similar materials having sufficient strength and flexibility.

As used herein, "proximal" is closest to the operator of the device and "distal" will typically be away from the operator and toward the patient when the device is in use.

Figure 4A:
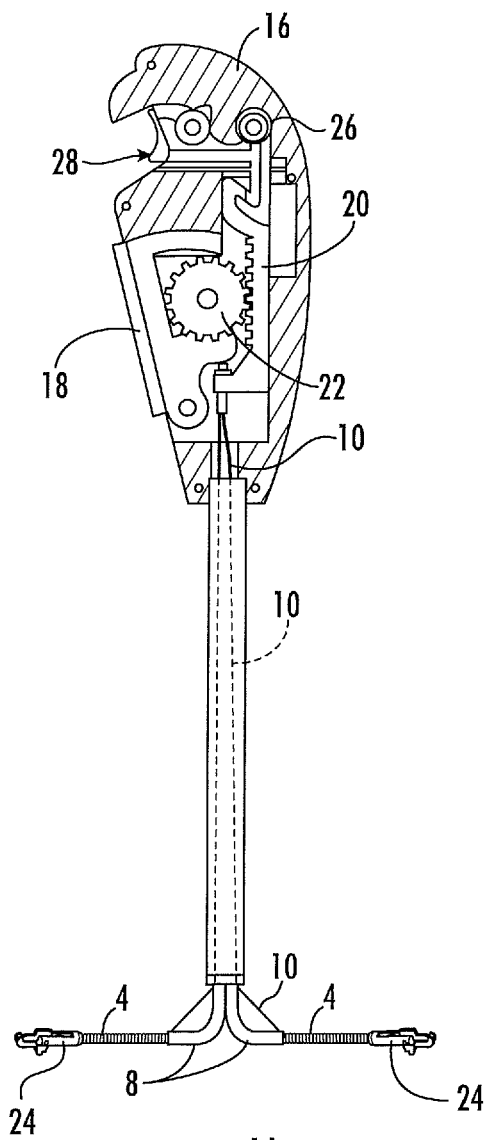
FIG. 4A is a sectioned view in an embodiment similar to that of FIG. 1 showing the actuation mechanism for extending and retracting the flexible arms with the flexible arms extended.
Figure 4B:
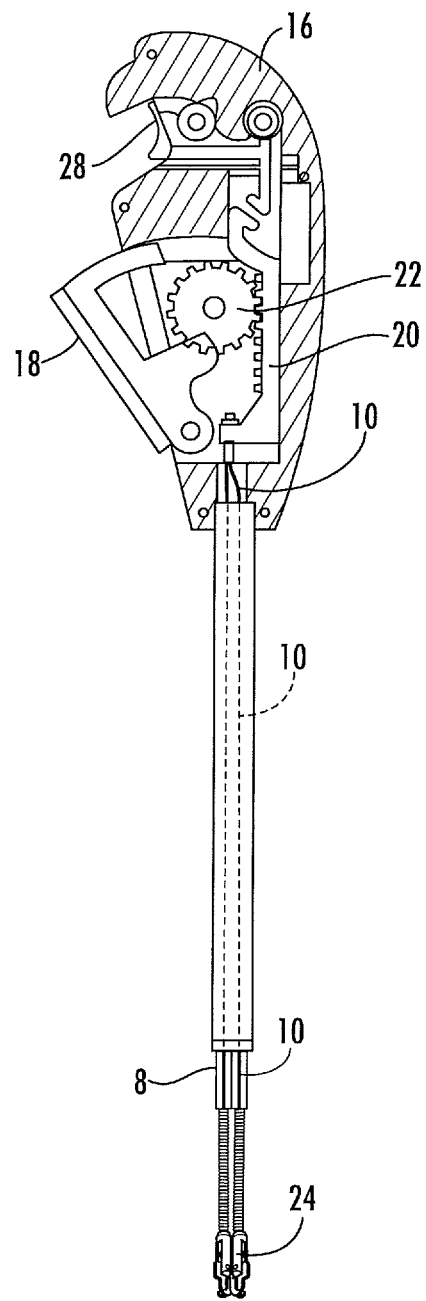
FIG. 4B is a sectioned view of the embodiment of the invention shown in FIG. 4A with the flexible arms retracted.

The actuator construct shown in FIG. 4A and FIG. 4B pulls the control wires 10, moving the flexible arms 4 to form a radial array (FIG. 2). This action unfolds the graft to a spread and generally planar position. In a preferred embodiment, when the travel of the actuator lever 18 is fully exhausted, the flexible arms may be positioned at an angle of somewhat more than 90° from the axis of travel of the actuator, or the central axis of the shaft. FIG. 14 shows the flexible arms as positioned at an angle of more than 90° from the central axis of the shaft. In some embodiments, this angle could be up to 120° from the generally parallel position of the flexible arms shown in FIG. 1. The actuator may be designed to allow the operator to set the desired angle. In some embodiments, the angle may be at least 100° and perhaps more, so that the edges, or periphery, of the graft are pulled against the defect of the patient for subsequent securing or suturing of the graft.

According to one embodiment of the invention, the device may comprise a housing 16 having a trigger or actuator lever 18. The housing may form a housing for the mechanism of the invention, including the actuator construct for the control wires 10. At the distal end of the device is the plurality of spaced-apart flexible arms 4 that terminate at the connectors for the graft, which may be grasping jaws 24.

The flexible arms 4 are preferred to be formed of a flexible cable. The cable may be a hollow cable formed of coiled or spirally-wound material which is capable of repetitive flexing and bending. The cable may comprise stainless steel suitable for use in surgical applications. The cables are sufficiently flexible to form the radial array shown in FIG. 2 when a force is applied by the control wires to the sleeves 8, but return to a flaccid condition as shown in FIG. 1 as the control wires cease pulling the flexible arms to the radial array. The flexible arms are preferred to be flexible along their entire length, without having preformed bends or angles that may tend to dictate a path of travel as the flexible arms are withdrawn from the surgical site. The flexible cables used with the sleeves (that are also flexible) and the control wires allow the cables to follow the anatomical structure or host tissue, or a trocar, as a path of travel as the flexible arms are pulled away from the graft. The sleeves may also be formed of hollow cable that is constructed and arranged to surround the flexible arms as shown in the drawing figures. Rigid members, rather than flexible cables, may tend to resist removal, due to anatomical structure or host tissue interfering with the path of travel. The flexible arms and the sleeves are preferred to have shape memory that allows them to return to about the shape shown in FIG. 1 or FIG. 14A when the control wires are not actuated to apply a force upon the flexible arms, The embodiment as shown in FIGS. 1 and 2 has four (4) flexible arms 4. At least three (3), and preferably four (4) or more, flexible arms are employed. The flexible arms must be able to deploy and spread out the graft for attachment to tissue as shown in FIG. 14C.

The flexible arms are formed in a radial array by force applied by the plurality of control wires 10. One control wire is associated with each flexible arm. The control wires pull against the sleeves 8 and the flexible arms to form the radial array. FIG. 2. As shown in FIG. 1, the flexible arms are substantially parallel to each other as they extend from shaft 6 of housing 16. No substantial tension is applied to the control wires in this configuration. The device with graft attached may be inserted into the surgical site incision in this configuration.

In FIG. 2, the control wires 10 are actuated to pull against the sleeves 8, forming the flexible arms 4 into a radial array. In use, the graft 2 is positioned on the flexible arms and the graft expanded for attachment by movement of the flexible arms into the radial array.

In an embodiment as shown in FIGS. 4A and 4B, the control wires are actuated simultaneously by the actuator construct contained in housing 16. An actuation lever 18 engages and rotates the ideal gear 22. The ideal gear 22 moves the rack gear 20 upwardly, applying a pulling pressure to the control wires 10 to form the flexible arms into the radial array. The ideal gear and the rack gear form a rack and pinion construct.

Latch 26 has interlocking members that engage with each other to hold the flexible arms in the radial array when the rack gear reaches its fully upward position. The interlocking members each comprises hook that interlocks with the corresponding hook. The graft is thereby held in a position for surgical attachment. A flexible arm release lever 28 pushes an interlocking member of the latch away from an interlocking member that may be formed on the rack gear 20 to release the control wires. With no tension or pulling force on the control wires, the flexible arms return to generally the position of FIG. 1. With tension released on the control wires, the flexible arms may be withdrawn through a trocar and/or surgical incision.

Figure 3:
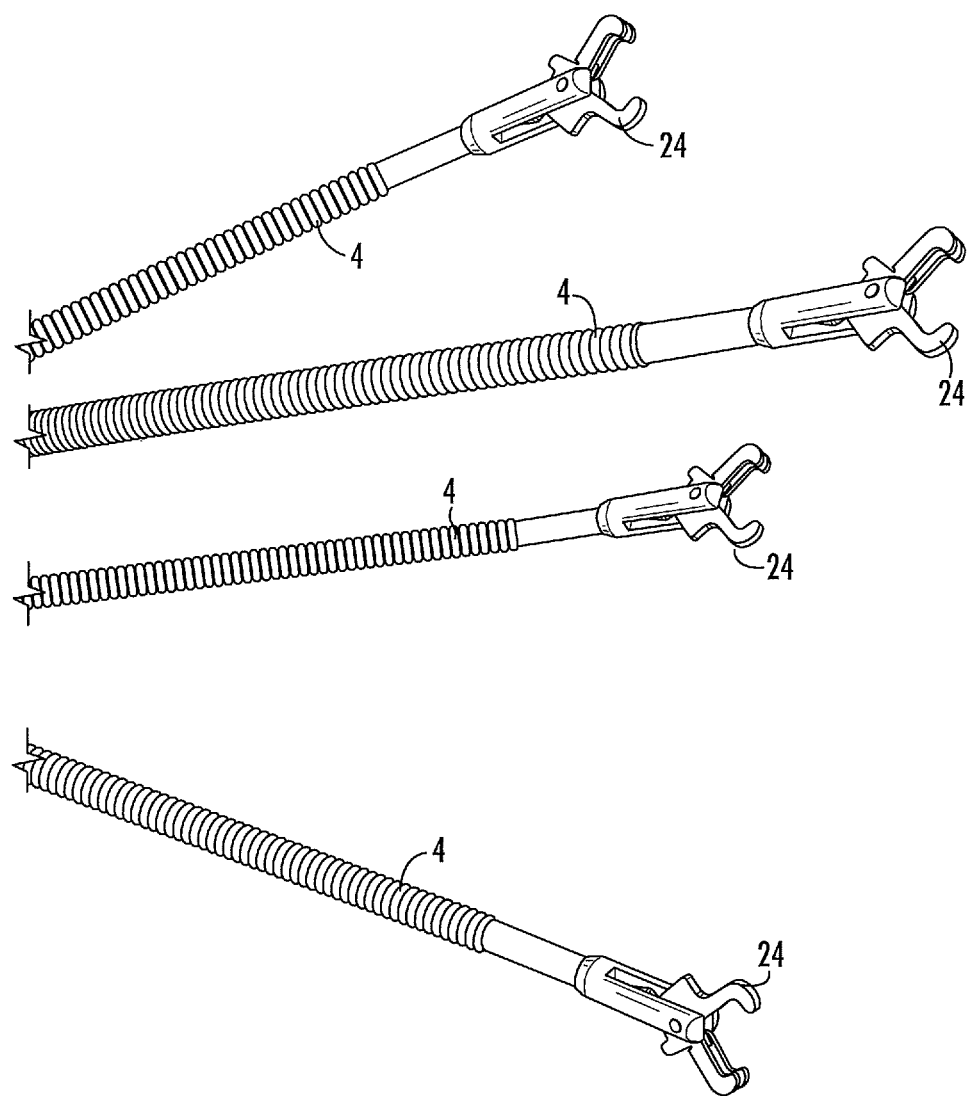
FIG. 3 shows flexible arms of the embodiment of FIG. 1 with the grasping jaws 24 at an end of each flexible arm in an open position for receiving a graft.

In the embodiment of the device shown in FIGS. 1 through 3, connectors 24 are positioned at or near the end of the flexible arms and are used to hold the graft for deployment. The connectors close upon the graft 2 to hold the graft. The connectors may be in the form of grasping jaws 24 in one embodiment that are actuated to close and open by pulling and releasing a connector strand, which may be a wire activation cable, or pull wire 56. A connector actuator construct as shown in FIG. 7, FIG. 8 and FIG. 10 communicates with the pull wire to open and close the connectors or grasping jaws for attachment and release of the graft. The connector actuator comprises a shuttle 40 in a preferred embodiment that ends with a control button 30 that extends from an end of the housing. The control button may be unitary with the shuttle, since depressing the control button (FIG. 8) moves the shuttle to open the connectors or grasping jaws. In this embodiment, each control button and shuttle is associated with one flexible arm 4 and its associated grasping jaw. Each control button is associated with one grasping jaw. Actuating, or depressing, a control button associated with a grasping jaw causes it to open. Preferably, the control buttons are formed to individually lock the grasping jaws in an open position when the control button in depressed (FIG. 3).

Figure 5:
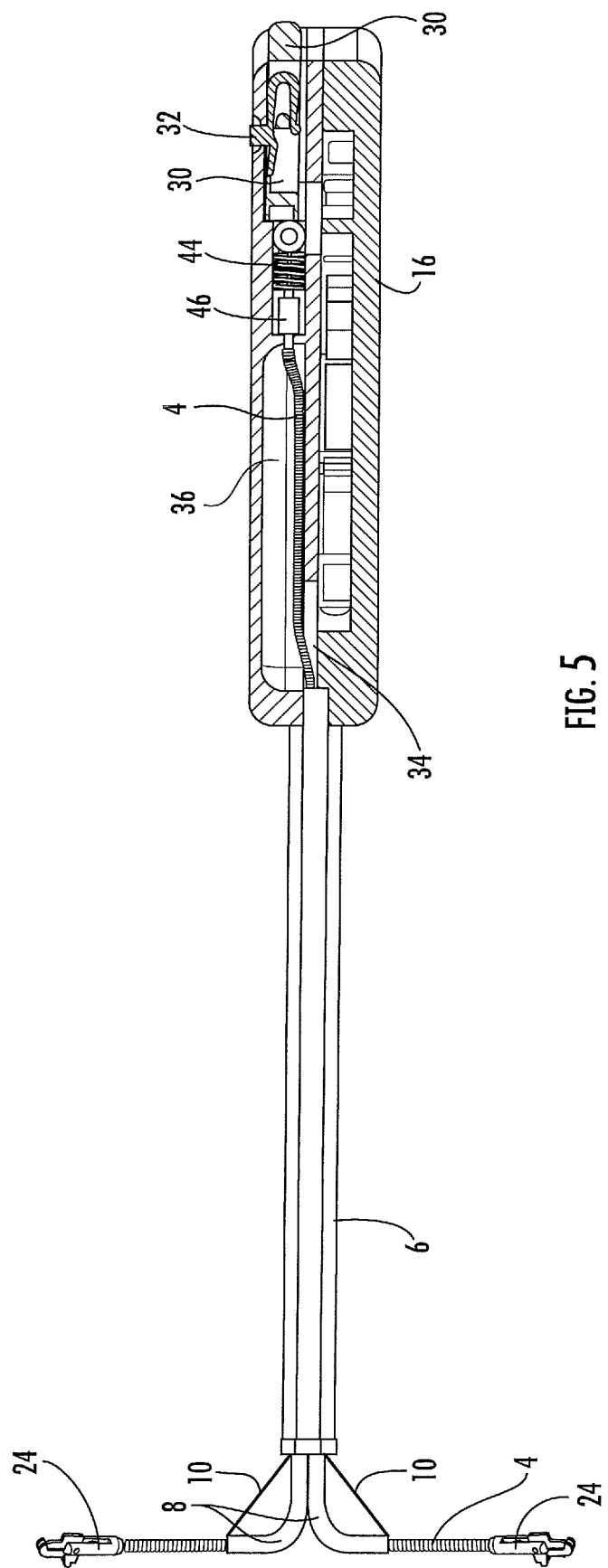
FIG. 5 is a sectioned view of an embodiment of the invention showing actuators in housing 16.

FIG. 5 is a top, sectioned view of the housing 16, showing two compartments, with one compartment on each side. The compartments may be separated by a divider 34. The lower compartment of the housing, when viewing FIG. 5, contains the mechanism of FIG. 4A and FIG. 4B and applies a force to sleeves 8 by control wires 10. This mechanism actuates the flexible arms 4 to pull the flexible arms into the radial array, or release the flexible arms.

The upper side of the housing as shown in FIG. 5 has a cavity 36 to store a portion of the flexible arms as the length of the flexible arms is adjusted for the specific application of a graft. The length of the flexible arms 4 may be adjusted by manually pulling or pushing the flexible arms into or out of the housing 16. Cavity 36 of the housing stores excess length of the flexible arms. The length adjustment feature is useful to adjust the size of the arm array to the dimensions, and particularly the perimeter, of the graft, so that the radial array of the device fits the graft and pulls the graft tight, but not tight enough to deform the flexible arms of the radial array. A frictional braking device 38 (FIG. 6B) is preferred to be positioned near the entry/exit of the cavity 36 of the housing to apply friction to the flexible arms. The frictional braking device applies friction to each flexible arm that is sufficient to allow a length of each of the flexible arms to be pushed into or pulled from the housing, while preventing unwanted withdrawal or insertion of the flexible arms relative to the housing. The frictional braking device may be opposing sheets of vinyl, rubber, or similar compressible materials through which the flexible arms pass, and which applies a frictional force on the flexible arms. In a preferred embodiment, the frictional braking device has openings or conduits equal in number to the number of flexible arms. Each flexible arm engages one of the conduits and the conduit applies a frictional force to the flexible arm to retard but not prevent movement of the flexible arm into and out of the cavity as described. A cover of the housing may have protrusion(s) or boss(es) 72 formed thereon that applies pressure to deform the braking device and conduits for the application of frictional pressure to the flexible arms.

By the control wires 10 acting on the sleeves, with the flexible arms 4 being slidable relative to the sleeves 8, the length of the portion of the flexible arms that extend from the distal end of the device may be altered while still providing a workable mechanism for forming the radial array irrespective of the length of each flexible arm that is chosen. Separate mechanisms are provided for controlling the length of the flexible arms and opening and closing of the grasping jaws on one side of the housing 16 and the actuation of the sleeves to form the radial array on the other side of the housing.

The graft 2 is attached about its perimeter to each of the flexible arms 4. The graft is attached at spaced apart intervals so that the graft is formed in a radial array when the control wires are actuated. A portion of the graft is inserted between each open connector, which is a grasping jaw 24 in the embodiment shown. After insertion of a portion of the graft into the open grasping jaw, the grasping jaw is closed by releasing tension on the connector strand to hold the graft. The control buttons 30 are released from their locked positions by one or more release buttons 32. FIG. 10A, 10B. In a preferred embodiment, the grasping jaws 24 each have a separate control button 30 and release button 32 so that the grasping jaws can each be independently opened and closed.

FIG. 7 shows housing 16 with flexible arms 4 attached to the grasping jaws 24, and extending from the cavity 36 of the housing and though shaft 6. This construct communicates with control buttons 30 to open the grasping jaws, which are normally closed. Anchor sites 46 for the flexible arms 4 are shown.

FIG. 8 is enlarged to show the detail of a preferred structure of the anchor sites. Shuttle 40 communicates with an associated control button 30. A set screw 42 connects pull wire 56 to the shuttle. A compression spring 44 tensions the control wire to hold the grasping jaw closed. An anchoring collar 46 for the flexible arm is provided. Depressing release button 32 (FIG. 10B) allows the shuttle to be pushed proximally to compress the spring 44 and close the grasping jaws by providing tension on the pull wire.

FIG. 9 shows detail of an embodiment of the grasping jaws 24. The grasping jaws may have an upper tooth 48 and a lower tooth 50 as shown, each of which pivot about a pivot pin 52. The upper tooth and the lower tooth may be housed in the jaw housing 54. A pair of pull wires 56 that may be internal to the flexible arm 4 contract to open and close. The grasping jaws are preferred to be normally closed. Springs 44 apply tension to the pull wires so that the grasping jaws are closed until the shuttle 40 via control buttons 30 push the springs forward to relieve tension on the pull wires.

FIGS. 10A, 10B show the interaction between an embodiment of the shuttle 40 and release button 32. As shown in FIG. 10A, the shuttle is pushed forward by pressing control button 30. This action depresses spring 44 and opens the grasping jaw. An end of release button 32 engages an opening in the shuttle due to shape memory properties of the release button, locking the shuttle in place with the grasping jaw open.

Depressing release button 32 disengages the end of the release button. Spring 44 causes the shuttle to move from the position of FIG. 10A to the position of FIG. 10B. Expanded spring 44 applies tension to the pull wires 56 to close the grasping jaws 24. In the embodiment shown, a release button 32 is provided for each flexible arm and associated grasping jaw. However, a bridge could be provided so that the grasping jaws may be universally closed at once. After the grasping jaws are closed on the graft 2, the graft is held in place by the grasping jaws 24. After surgical attachment of the graft, the control buttons are actuated to release the graft from the grasping jaws. The control wires 10 are also released from tension by the actuator construct, and the device is removed through the surgical site incision.

FIG. 12 demonstrates the graft being attached to the device. The grasper jaws are opened using the control buttons 30. In this embodiment, the graft is connected at four (4) points to the flexible arms using the grasper jaws and generally about the perimeter of the graft. The grasper jaws are closed on the graft to hold the graft. The actuator is used to place the flexible arms in an orientation with the flexible arms generally parallel to each other for insertion through a trocar and into the surgical site.

A sheath 64 for facilitating insertion of the flexible arms and graft into the trocar and to the surgical site is shown. FIGS. 13A-13D. The sheath in this embodiment is a split tube that may be transparent or translucent. The sheath is preferred to be tapered, or have a frusto-conical shape that tapers or progressively reduces in diameter from left to right when viewed as in the drawing figures. A stand 68 holds an end of the sheath open at the split. A bullet shaped tool 66 having a diameter that is larger than the middle of the sheath may be used to slide from the end of the sheath that is adjacent to the stand and along the sheath to the opposite end, forcing the sheath to open about the split. FIG. 13B. The sheath is open at the split to a width that permits insertion of the flexible arms and the graft. The sheath, attached to the device, is placed into the sheath through the split. The sheath and the device are removed from the stand for insertion into a trocar.

FIGS. 11A, 14A show a seal 62 mounted to the shaft 6. The seal engages the trocar and the shaft to form a seal, inhibiting gases from escaping the belly of the patient. FIG. 14B. An O-ring may be present about a circumference 70 of the seal to improve sealing.

In use, according to one embodiment, a section of graft 2 of appropriate size to repair the subject hernia is selected and/or formed. FIG. 12. The graft may be formed (of various biological materials or, synthetic materials, including, but not limited to polypropylene or polytetrafluoroethylene (PTFE). The graft is connected near its perimeter to the connectors near the distal ends of the flexible arms. Each flexible arm is preferred to have a connector, such as grasping jaws 24. The activation lever 18 is in the position shown in FIG. 1, with the flexible arms positioned generally parallel to the axis of travel of the actuator. The graft is held by the flexible arms and folded. The graft is preferred to be covered by the sheath 64 for insertion into the trocar.

An incision in tissue 84 of the patient is made at the approximate center of the defect. Preferably, a trocar 82 is present within the incision. FIGS. 14A-C. The flexible arms of the device in a generally parallel orientation are inserted through the approximate center of the defect. FIG. 14A. The sheath 64 facilitates insertion of the graft 2 into the trocar, and protects the graft as it moves through the trocar to the surgical site. FIG. 14B. After the distal end of the device with graft attached travels through the trocar, and sufficient clearance through the defect 80 is obtained, the actuator, such as the gear train of FIG. 4A, is actuated causing the actuator to pull the control wires 10, the flexible arms 4 and associated graft to the position shown in FIG. 14. The graft is pulled up against the tissue by means of the handle of the device to cover the hernia defect 80. Graft attachment to the tissue may be provided by known methods of attachment of grafts at surgical sites such as hernia defects. The procedure may be monitored by use of a laparoscope for proper positioning, and securing, of the graft.

The graft is formed to generally a planar form when the flexible-arms form the radial array. As noted, the flexible arms may move through an arc that is more than 90°. Therefore, the surface of the graft may be somewhat curved or non-planar, so that the edges or periphery of the graft is pushed against the tissue and secured to the tissue to cover the defect. However, the graft is still considered to be in a generally planar position.

After the connectors 24 are released from the graft as described above, tension is released from the control wires 10. The flexible arms return to the position shown in FIG. 1, FIG. 14A. The device may now be removed by pulling it upwardly through the trocar and away from the incision. The flexible arms, by being flexible along their length, with no preformed angles, kinks or similar geometry, are sufficiently flexible to follow a path of retreat from the fully extended position of FIG. 2 to the position shown in FIG. 1, without disrupting the sutured graft, while also being sufficiently rigid to support the graft for positioning and securement at the defect site.

What is claimed is:

1. A device for delivery of a graft for attachment to tissue, comprising:
    a plurality of flexible arms;
    an actuator, wherein the plurality of flexible arms is in communication with and moves in response to movement of the actuator, wherein movement of the actuator pulls the plurality of flexible arms into a radial array wherein distal ends of the plurality of flexible arms extend from a shaft and spread away from each other to form the radial array;
    wherein each of the plurality of flexible arms is slidable relative to the shaft, and a length of each of the plurality of flexible arms that extends from the shaft is individually adjustable by sliding of a flexible arm of the plurality of flexible arms relative to the shaft, wherein a length of a first arm of the plurality of the flexible arms that forms the radial array is differentiated from a length of a second arm of the plurality of flexible arms that forms the radial array.

2. A device for delivery of a graft for attachment to tissue as described in claim 1, further comprising a brake, wherein each of the plurality of flexible arms frictionally engages the brake, and wherein the brake permits the plurality of flexible arms to slide relative to the shaft to permit individual adjustability of the plurality of flexible arms and the brake resists sliding of the plurality of flexible arms relative to the shaft when the plurality of flexible arms form the radial array.

3. A device for delivery of a graft for attachment to tissue as described in claim 1, further comprising a brake, wherein the brake comprises a plurality of channels formed therein, and each of the plurality of flexible arms frictionally engages a channel of the plurality of channels of the brake, and wherein the brake permits the plurality of flexible arms to slide relative to the shaft to permit individual adjustability of the plurality of flexible arms and the brake resists sliding of the plurality of flexible arms relative to the shaft when the plurality of flexible arms form the radial array.

4. A device for delivery of a graft for attachment to tissue as described in claim 1, wherein a portion of each of the plurality of flexible arms is slidable into a chamber of a housing, wherein the chamber is of sufficient size and constructed to receive a flexed portion of the plurality of flexible arms.

5. A device for delivery of a graft for attachment to tissue as described in claim 1,
    the plurality of flexible arms comprising three flexible arms,
    wherein each of the three flexible arms comprises a connector at the distal end of each of the three flexible arms, and
    wherein each connector is constructed to open and close, and each connector is constructed to close on a graft, and the three flexible arms hold the graft in the radial array when the actuator pulls the plurality of flexible arms into the radial array.

6. A device for delivery of a graft for attachment to tissue as described in claim 1,
    the plurality of flexible arms comprising three flexible arms, wherein each of the three flexible arms comprises a connector at the distal end of each of the three flexible arms, and
    wherein each connector is constructed to open and close, and each connector is constructed to close on a graft, and the connectors and the three flexible arms hold the graft in the radial array when the actuator pulls the plurality of flexible arms into the radial array, and
    wherein each connector of each of the three flexible arms is constructed to open and close separately from every other connector.

7. A device for delivery of a graft for attachment to tissue as described in claim 1, the plurality of flexible arms comprising three flexible arms, wherein each of the three flexible arms comprises a connector at the distal end of each of the three flexible arms, and wherein each connector is constructed to open and dose, and each connector is constructed to dose on a graft, and the connectors and the three flexible arms hold the graft in the radial array when the actuator pulls the plurality of flexible arms into the radial array, and wherein each connector of each of the three flexible arms is constructed to open and dose separately from every other connector, and a housing in which the actuator is contained comprising three connector actuators, wherein dosing of each connector is remotely actuated by a corresponding connector actuator of the three connector actuators, and each of the three connector actuators operates independently of each of the other connector actuators and independently of the actuator that pulls the plurality of flexible arms into the radial array.

8. A device for delivery of a graft for attachment to tissue as described in claim 1, the plurality of flexible arms comprising three flexible arms, wherein each of the three flexible arms comprises a connector at the distal end of each of the three flexible arms, and wherein each connector is constructed to open and close, and each connector is constructed to close on a graft, and the connectors and the three flexible arms hold the graft in the radial array when the actuator pulls the plurality of flexible arms into the radial array, and wherein each connector of each flexible arm of the three flexible arms is constructed to open and close separately from every other connector, and a housing in which the actuator is contained comprising three connector actuators, wherein opening of each connector is remotely actuated by a corresponding connector actuator of the three connector actuators, and each of the three connector actuators operates independently of each of the other connector actuators and independently of the actuator that pulls the plurality of flexible arms into the radial array, and wherein the housing comprises a release actuator, wherein the release actuator actuates tension on a connector linkage and causes the connector to close.

9. A device for delivery of a graft for attachment to tissue as described in claim 1, wherein the actuator comprises a rack and pinion, and rotation of the pinion by a lever actuates movement of the rack, and wherein the rack communicates with the plurality of flexible arms and movement of the rack forms the plurality of flexible arms into the radial array.

10. A device for delivery of a graft for attachment to tissue as described in claim 1, further comprising a sheath positioned at an end of the shaft and having a longitudinal split along a length thereof, wherein the sheath R constructed to accommodate and surround the distal ends of the plurality of flexible arms positioned generally parallel to each other and a graft connected to the plurality of flexible arms.

11. A device for delivery of a graft for attachment to tissue as described in claim 1, the plurality of flexible arms comprising three flexible arms and a connector at the distal end of each of the three flexible arms, wherein each connector is constructed to open and close, and each connector is constructed to close on a graft, the device for delivery of a graft for attachment to tissue further comprising a sheath having a longitudinal split along a length thereof, wherein the sheath is constructed to accommodate and surround the distal ends of the three flexible arms and a graft connected to the three flexible arms; and wherein the distal ends of each of the three flexible arms are positioned within the sheath in a generally parallel relationship, and the sheath is constructed and arranged to be inserted into a trocar.

12. A device for delivery of a graft for attachment to tissue, comprising:

a plurality of flexible arms and a plurality of sleeves, wherein each sleeve of the plurality of sleeves surrounds a portion of one of the flexible arms of the plurality of flexible arms;

an actuator, wherein the plurality of sleeves are in communication with and move in response to movement of the actuator, wherein movement of the actuator moves the plurality of sleeves and each sleeve of the plurality of sleeves moves the flexible arm it surrounds, and movement of the actuator forms the plurality of flexible arms into a radial array, wherein distal ends of the plurality of flexible arms extend from a shaft and spread away from each other to form the radial array;

wherein each of the plurality of flexible arms is slidable relative to the sleeve that surrounds it and a length of a portion of each of the plurality of flexible arms that extends distally from the sleeve that surrounds it is adjustable by sliding the plurality of flexible arms relative to the plurality of sleeves, wherein a length of a first arm of the plurality of flexible arms that extends from a first sleeve of the plurality of sleeves is variable relative to a length of a second arm of the plurality of flexible arms that extends from a second sleeve of the plurality of sleeves.

13. A device for delivery of a graft for attachment to tissue as described in claim 12, further comprising a brake, wherein each of the plurality of flexible arms frictionally engages the brake and wherein the brake permits the plurality of flexible arms to slide relative to the plurality of sleeves to permit individual adjustability of the plurality of flexible arms and the brake resists sliding of the plurality of flexible arms relative to the plurality of sleeves when the plurality of flexible arms form the radial array.

14. A device for delivery of a graft for attachment to tissue as described in claim 12, further comprising a brake, wherein the brake comprises a plurality of channels formed therein, and each of the plurality of flexible arms frictionally engages a channel of the plurality of channels of the brake and wherein the brake permits the plurality of flexible arms to slide relative to the plurality of sleeves to permit individual adjustability of the plurality of flexible arms and the brake resists sliding of the plurality of flexible arms relative to the plurality of sleeves when the plurality of flexible arms form the radial array.

15. A device for delivery of a graft for attachment to tissue as described in claim 12, wherein a portion of each of the plurality of flexible arms is slidable into a chamber of a housing, wherein the chamber is of sufficient size and constructed to receive a flexed portion of the plurality of flexible arms.

16. A device for delivery of a graft for attachment to tissue as described in claim 12, the plurality of flexible arms comprising three flexible arms, wherein each of the three flexible arms comprises a connector at the distal end of each of the three flexible arms, and wherein each connector is constructed to open and close, and each connector is constructed to close on a graft, and the three flexible arms hold the graft in the radial array when the actuator pulls the plurality of sleeves to form the plurality of flexible arms into the radial array.

17. A device for delivery of a graft for attachment to tissue as described in claim 12,
the plurality of flexible arms comprising three flexible arms, wherein each of the three flexible arms comprises a connector at the distal end of each of the three flexible arms, and
wherein each connector is constructed to open and close, and each connector is constructed to close on a graft, and the connectors and the three flexible arms hold the graft in the radial array when the actuator pulls the plurality of sleeves to form the plurality of flexible arms into the radial array, and
wherein each connector of each of the three flexible arms is constructed to open and close separately from every other connector.

18. A device for delivery of a graft for attachment to tissue as described in claim 12,
the plurality of flexible arms comprising three flexible arms,
wherein each of the three flexible arms comprises a connector at the distal end of each of the three flexible arms, and wherein each connector is constructed to open and dose, and each connector is constructed to dose on a graft, and the connectors and the three flexible arms hold the graft in the radial array when the actuator pulls the plurality of sleeves to form the plurality of flexible arms into the radial array, and
wherein each connector of each of the three flexible arms is constructed to open and dose separately from every other connector, and
a housing in which the actuator is contained comprising three connector actuators, wherein dosing of each connector is remotely actuated by a corresponding connector actuator of the three connector actuators, and each of the three connector actuators operates independently of each of the other connector actuators and independently of the actuator that pulls the plurality of sleeves to form the plurality of flexible arms into the radial array.

19. A device for delivery of a graft for attachment to tissue as described in claim 12,
the plurality of flexible arms comprising three flexible arms, wherein each of the three flexible arms comprises a connector at the distal end of each of the three flexible arms, and
wherein each connector is constructed to open and close, and each connector is constructed to close on a graft, and the connectors and the three flexible arms hold the graft in the radial array when the actuator pulls the plurality of sleeves to form the plurality of flexible arms into the radial array, and wherein each connector of each of the three flexible arms of the plurality of flexible arms is constructed to open and close separately from every other connector, and
a housing in which the actuator is contained comprising three connector actuators, wherein opening of each connector is remotely actuated by a corresponding connector actuator of the three connector actuators, and each of the three connector actuators operate independently of each of the other connector actuators and independently of the actuator that pulls the plurality of sleeves to form the plurality of flexible arms into the radial array, and
wherein the housing comprises a release actuator, wherein the release actuator actuates tension on a connector linkage and causes the connector to close.

20. A device for delivery of a graft for attachment to tissue as described in claim 12, wherein the actuator comprises a rack and pinion, and rotation of the pinion by a lever actuates movement of the rack, and wherein the rack communicates with the plurality of sleeves to simultaneously form the flexible arms into the radial array.

21. A device for delivery of a graft for attachment to tissue as described in claim 12, further comprising a sheath positioned at an end of the shaft and having a longitudinal split along a length thereof, wherein the sheath is constructed to accommodate and surround the distal ends of the plurality of flexible arms positioned generally parallel to each other and a graft connected to the plurality of flexible arms.

22. A device for delivery of a graft for attachment to tissue as described in claim 12,
the plurality of arms comprising three flexible arms and,
wherein each of the three flexible arms comprises a connector is constructed to open and close, and each connector is constructed to close on a graft,
the device for delivery of a graft for attachment to tissue further comprising a sheath having a longitudinal split along a length thereof,
wherein the sheath is constructed to accommodate and surround the distal ends of each of the three flexible arms positioned generally parallel to each other and a graft connected to each of the three flexible arms and the sheath is constructed and arranged to be inserted into a trocar.

23. A device for delivery of a graft for attachment to tissue as described in claim 12, further comprising a brake, wherein the brake comprises a plurality of channels formed therein, and each of the plurality of flexible arms frictionally engages a channel of the plurality of channels of the brake and wherein the brake permits the plurality of flexible arms to slide relative to the plurality of sleeves to permit individual adjustability of the plurality of flexible arms and the brake resists sliding of the plurality of flexible arms relative to the plurality of sleeves when the plurality of flexible arms are positioned generally parallel to each other and travel through a trocar.

* * * * *